United States Patent [19]

Daikuzono

[11] Patent Number: 5,174,297
[45] Date of Patent: Dec. 29, 1992

[54] DIAGNOSTIC APPARATUS FOR LIVING TISSUES AND MEDICAL TREATMENT APPARATUS WITH DIAGNOSTIC APPARATUS

[75] Inventor: Norio Daikuzono, Chiba, Japan
[73] Assignee: S.L.T. Japan Co., Ltd., Tokyo, Japan
[21] Appl. No.: 616,274
[22] Filed: Nov. 20, 1990
[30] Foreign Application Priority Data
Nov. 22, 1989 [JP] Japan .................. 1-303562
[51] Int. Cl.⁵ .................................. A61B 5/00
[52] U.S. Cl. .................................. 128/665; 606/3; 606/10; 606/16
[58] Field of Search ............ 128/665, 654, 397, 398; 606/3, 15, 16, 10

[56] References Cited

U.S. PATENT DOCUMENTS

| 4,612,938 | 9/1986 | Dietrich et al. | 128/665 |
| 4,641,650 | 2/1987 | Mok | 128/665 |
| 4,693,244 | 9/1987 | Daikuzono | |
| 4,736,743 | 4/1988 | Daikuzono | |
| 4,768,513 | 9/1988 | Suzuki | 128/665 |
| 4,913,142 | 4/1990 | Kittrell et al. | 606/15 |

FOREIGN PATENT DOCUMENTS 63-216579 9/1988 Japan .
2-34161 2/1990 Japan .

OTHER PUBLICATIONS

Markus, *Electronics Dictionary*, 4th Ed. (McGraw Hill 1978), p. 289.

Primary Examiner—Ruth S. Smith
Attorney, Agent, or Firm—Lowe, Price, LeBlanc & Becker

[57] ABSTRACT

Diagnostic apparatus for diagnosing the location and the size and the like of cancer tissues. Laser light emitted from a laser light generator is impinged into a first spectroscope and a specific spectrum can be selected from the impinged laser light by the first spectroscope. This specific spectrum is transmitted to the target area of the tissues by a laser light transmitting system. The transmitted spectrum is reflected at the target area to produce a reflected wave. A spectrum can be selected from the reflected wave by a second spectroscope. This spectrum can be detected by a spectrophotometer. The laser light emitted from the laser light generator can be also irradiated against the target area for carrying out treatment and diagnosis simultaneously.

8 Claims, 3 Drawing Sheets

DIAGNOSTIC APPARATUS FOR LIVING TISSUES AND MEDICAL TREATMENT APPARATUS WITH DIAGNOSTIC APPARATUS

BACKGROUND OF THE INVENTION

1. Field of the Invention

This invention relates to diagnostic apparatus for diagnosing the location and the size of living tissues, particularly of cancer tissues, with laser light irradiation, and relates to medical treatment apparatus for treating the tissues on the basis of information detected from the diagnostic system.

2. Prior Art

In order to carry out medical treatments for cancer tissues, thermal therapies and laser-chemical therapies with laser light have been commonly utilized. In order to perform these therapies efficiently, it is important to detect precisely the information about the cancer tissues such as its location, and its size.

It is known that, when the laser light is irradiated against the cancer tissues, characteristic fluorescene is emitted from the cancer tissues and that, when a photoreactant (hematoporphyrin derivative, pheophobide A etc.) is absorbed into the cancer tissues, other characteristic fluorescence is emitted from the cancer tissues. Therefore, the tissues emitting the fluorescence should be detected as the cancer tissues in order to know the information of the cancer tissues for carrying out effectively the medical treatment for the cancer tissues.

In the prior art, for detecting and diagnosing the cancer tissues, argon-dye laser light operated in a continuous wave mode is irradiated against the target area of the living tissues with a high output power level of about 200 MW in an irradiating system. A reflective wave from the cancer tissues is detected by means of a spectroscope in a detecting system, which is provided separately from the irradiating system.

However, this conventional method has the following problems.

First, in order to detect the size of the cancer tissues, the laser light should be irradiated against the tissues including the boundary portion between normal tissues and the cancer tissues as well as the cancer tissues themselves. Accordingly, by the laser light irradiation with high output power level, the normal tissues are often damaged.

Next, if enough of the characteristic fluorescence was emitted, the diagnosis of the cancer tissues could be carried out efficiently. However, from the boundary portion of the cancer tissues, not enough fluorescence is emitted. Further, noise produced in an emission lamp is mixed into the laser light emitted from a laser light generator. Thus, the laser light containing the noise is irradiated against the cancer tissues. Accordingly, the reflected wave from the tissues can not show the information of the tissues precisely. As shown in FIG. 3, which is a graphical view of the spectrum of the reflected wave from the cancer tissues with this conventional method, the spectrum having the wavelength of 670 nm produced by the fluorescence emission of the cancer tissues could not be detected at all. That is to say, although this conventional method can be performed theoretically, it can not be utilized practically because of the small amount of the fluorescence emission from the boundary portion and the mixing of the noise into the laser light.

On the other hand, the reflected wave might be amplified so that the spectrum having the wavelength of 670 nm produced by the fluorescence emission of the cancer tissues can be detected. However, according to the study of the inventor, in this case, it is also impossible to eliminate the influence of the noise to the spectrum.

SUMMARY OF THE INVENTION

It is therefore the main object of the present invention to provide diagnostic apparatus for diagnosing the cancer tissues by which a spectrum having the wavelength of 670 nm produced by the fluorescence emission of the cancer tissues can be detected precisely. Another object of the present invention is to provide medical treatment apparatus for treating the cancer tissues on the basis of information about the tissues detected from the diagnostic system.

According to the present invention, diagnostic apparatus for living tissues is provided. This apparatus is comprised of a first spectroscope, a laser light transmitting system, a second spectroscope and a photomultiplier. Laser light emitted from a laser light generator is impinged into the first spectroscope and a specific spectrum can be selected from the impinged laser light by the first spectroscope. This specific spectrum is transmitted to the target area of the living tissues by the laser light transmitting system. The transmitted spectrum is reflected at the target area of the tissues to produce a reflected wave. A spectrum can be selected from the reflected wave by the second spectroscope. This spectrum can be detected by the photomultiplier.

By providing laser light irradiation means to the above mentioned diagnostic apparatus, diagnostic and treatment apparatus for living tissues is provided. Therefore, the laser light emitted from the laser light generator can be irradiated against the target area of the living tissues for carrying out treatment and diagnosis simultaneously.

In the present invention, in order to eliminate the influence of the noise to the spectrum of the fluorescence emission, only the spectrum of the laser light having a specific frequency is selected by means of the first spectroscope so as to be irradiated against the target area of the living tissues. Therefore, the noise is not mixed into the reflected wave from the tissues. As a result, a spectrum having the wavelength of 670 nm produced by the fluorescence emission of the cancer tissues can be detected clearly.

Further objects and advantages of the present invention will be apparent from the following description, reference being made to the accompanying drawing wherein preferred embodiments of the present invention are clearly shown.

DESCRIPTION OF THE PREFERRED EMBODIMENT

Figure 1:
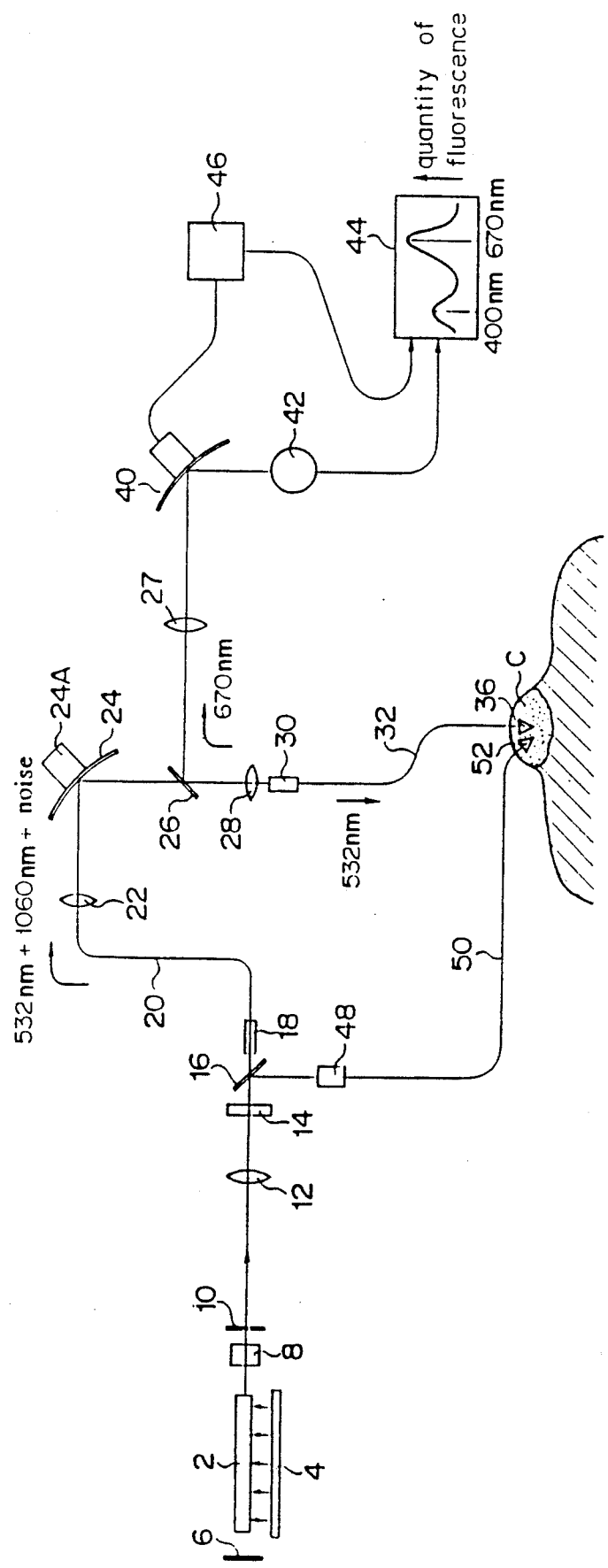
FIG. 1 is a schematic view of an embodiment of whole apparatus related to the present invention.

Now, the present invention will be described in more detail.

Laser light is emitted from a light source 4 such as a krypton lamp toward a laser oscillating rod 2 such as a Nd:YAG rod. Next, by means of a mirror 6 provided at the back of the rod 2, the laser light is directed, through the rod 2, toward a light switch 8 provided on the path of the laser light. Then, the laser light is pulsed by the light switch 8 such as a Q-switch. After the pulsed laser light goes through a partial transmissible mirror 10 and a lens 12, a second portion of the laser light having harmonics is removed by means of a second harmonic element 14.

Then, the rest of the laser light emitted from the element 14 is divided to reach a diagnostic irradiation system (toward a connecting member 18) and a treating irradiation system (toward a connecting member 48) respectively by a first dichroic partial mirror 16 for performing diagnosis and treatment separately. As will explained after, if the diagnosis and the treatment are performed in one system, this division by the first dichroic partial mirror 16 is not required.

The laser light in the diagnostic irradiation system passes, through a connecting member 18 and an optical fiber 20. Next, this laser light goes along the optical fiber 20 and, through a lense 22, and impinges on a first spectroscope 24 (laser spectral monochroic meter). A pulse motor 24A is provided at the back of the first spectroscope 24 for wavelength scanning. The suitable spectrum having a specific frequency is selected by the first spectroscope 24 operated by the pulse motor 24A. For example, if the spectrum having the wavelength of 532 nm is selected as the suitable spectrum, as explained after, this spectrum can be used also for a photo chemical treatment as well as for diagnosis. Then, the selected laser light goes through a second dichroic partial mirror 26, a lense 28 and a connecting member 30 and enters an optical fiber 32. This laser light continuously goes through the optical fiber 32 and is emitted from the fore end portion of the optical fiber 32 or from an emitting member provided at the fore end portion of the optical fiber 32 so as to be irradiated against the target area of tissues C.

Figure 2:
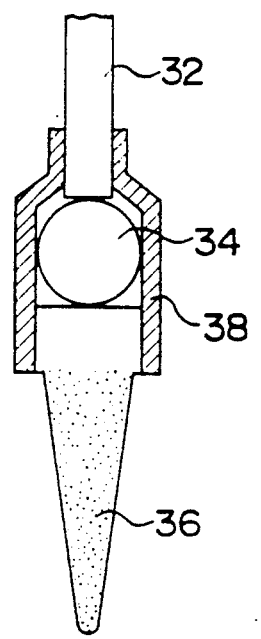
FIG. 2 is a longitudinal cross section of an embodiment of a laser light emitting member related to the present invention.
Figure 3:
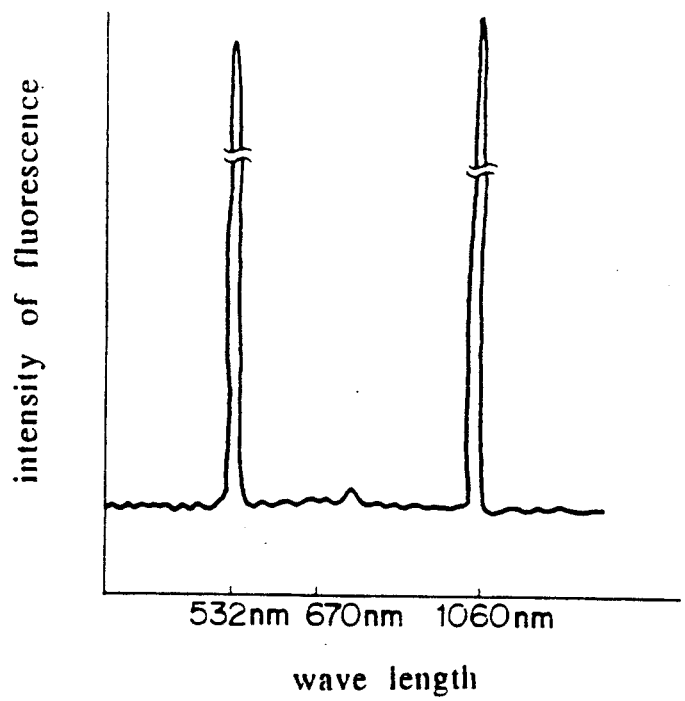
FIG. 3 is a graphical view of spectrum with a conventional method.

As shown in FIG. 2, the emitting member is composed of a condenser ball lens 34, a tapered conical probe 36, which is laser light transmissible and which is fabricated from a ceramic material, and a connecting holder 38, which connects the probe 36 and the optical fiber 32 and in which the condenser ball lens 34 is set so as to be disposed between the fiber 32 and the probe 36. The external surface of the probe is frosted or roughened for efficient laser light scattering.

On the other hand, a reflected wave from the tissues C is traced backward along the path of the laser light, which goes through the optical fiber 32 so as to be irradiated against the tissues C, until the second dichroic partial mirror 26. This reflected wave is partially divided by the mirror 26 to be directed toward a second spectroscope 40 through a lens 27. The spectrum of the divided reflected wave is selected by this second spectroscope 40 so as to be detected by a photomultiplier tube 42. Finally, as for the reflected wave from the tissues, a graphical view of the spectrum of the fluorescence emission is shown in a display 44. In this case, a pulse motor is attached to the spectrograph 40 for wavelength scanning. This pulse motor is driven by a pulse driver 46 so as to correspond to the result of the display 44.

If the tissues C are cancer tissues, fluorescence is emitted. Therefore, the spectrum having the wavelength of 670 nm is produced by the fluorescence emission. The graphical view of the spectrum is shown in the display 44. Further, if the photo-reactant is previously absorbed into the cancer tissues, other fluorescence is emitted. Then, another spectrum having another wavelength (in case of pheophobide A, the wave length is 400 nm) is produced by the other fluorescence emission. In the graphical view of the spectrum, there are two peaks at the wave lengths 400 nm and 670 nm respectively. As a result, since the intensity of the fluorescence emission can be known from the graphical view of the spectrum shown in the display 44, it will become apparent whether or not the tissues C are cancer tissues and the concentration level of the photo-reactant absorbed into the cancer tissues will become known.

While the diagnosis for the cancer tissues can be performed in this way, the medical treatment can be also performed with laser light irradiation means in one system simultaneously. When a Nd:YAG laser light is used, the inclination of the optical axis of the first spectroscope 24 is set so that a spectrum having the wavelength of 532 nm can be selected by the first spectroscope 24. In this case, it is preferred that the photo reactant be absorbed into the cancer tissues. Then, as explained before, this spectrum can be irradiated against the cancer tissues for a photochemical treatment. By this spectrum, the treatment as well as the diagnosis can be also performed. Alternatively, another spectrum having the wave length of 1060 nm can be used for a thermal therapy. Further, by the combination of these spectra, the photochemical treatment and the thermal therapy can be performed simultaneously together with the diagnosis. The diagnosis and the treatments can be performed with single laser light irradiation apparatus resulting in high availability. It is needless to say that the treatment system is not required in this case.

Alternatively, as explained before, the diagnosis system and the treatment system can be provided separately. In this case, for the treatment by laser light irradiation means of the treatment system, the spectrum is selected by the first dichroic partial mirror 16 and goes through the connecting member 48 to enter an optical fiber 50. Then, from the fore end portion of the optical fiber 50, directly or through a probe 52 which is the same type as the above mentioned probe 36, the laser light is irradiated against the cancer tissues. Thus, the treatment is performed in the treatment system, while the diagnosis is performed in the diagnosis system.

Although the laser light irradiated against the target area may be operated in a continuous wave mode, it is preferably operated in the pulse wave mode. Because, in case of the pulse wave mode, even if the average power level of the laser light is low, its peak power level is high, thus, enough fluorescence is emitted at every peak. For example, in case of the continuous wave mode, the fluorescence emission can be detected with the output power level of the laser light in the order of several hundreds milliwatt. On the other hand, in case of the pulse wave mode, even if in the order of the several milliwatt level, the fluorescence emission can be detected. Therefore, during the diagnosis and the treatment, the damage to the tissues can be decreased due to the low output power level of the laser light.

Figure 4:
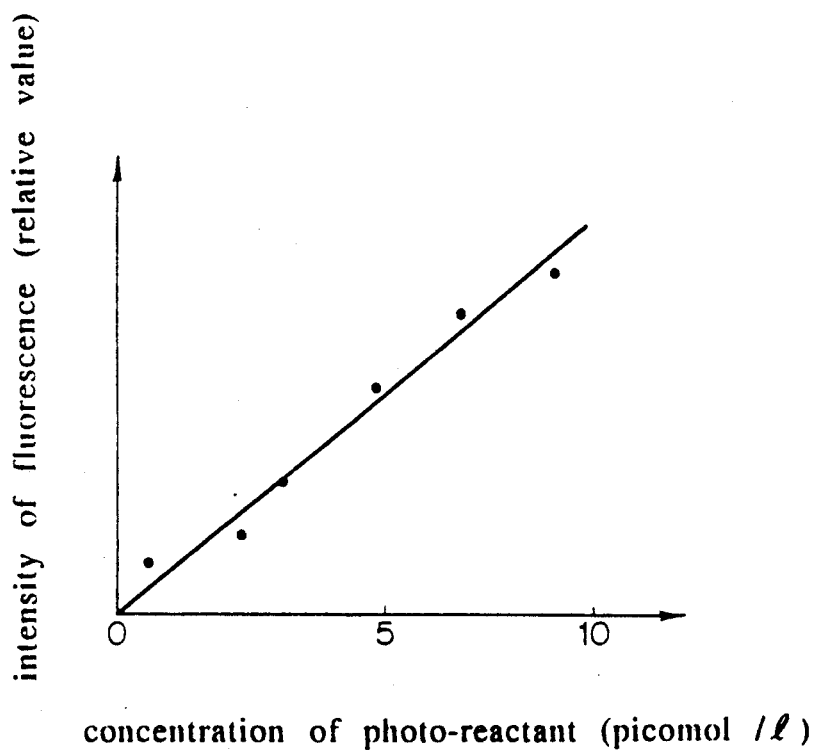
FIG. 4 is a graphical view showing the relation of the concentration of a photo-reactant with fluorescence intensity.

Further, according to the experiment of the inventor, as shown in FIG. 4, when the pheophobide A is used as the photo-reactant, the fluorescence emission can be detected with an extremely low concentration level of the pheophobide A of the order of picomol/liter.

While preferred embodiments have been described, it is apparent that the present invention is not limited to the specific embodiments thereof.

What is claimed is:

1. Diagnostic apparatus for living tissues, comprising:
   a laser light generator;
   a first spectroscope optically coupled to receive laser light emitted from the laser light generator, wherein said first spectroscope selectively outputs a specific spectrum from the laser light received from the laser light generator;
   a laser light transmitting system optically coupled to receive said specific spectrum output from said first spectroscope and transmit said specific spectrum to a target area of said living tissues;
   a second spectroscope arranged to optically receive light returned from said target area of said living tissues, wherein said second spectroscope selectively outputs a spectrum from the light returned from the target area; and
   means, receiving the output from the second spectroscope, for detecting the spectrum selected from light returned from the target area of said living tissues.

2. Diagnostic apparatus as in claim 1, wherein the laser light generator comprises a Nd:YAG laser.

3. Diagnostic apparatus as in claim 1, further comprising means for scanning the second spectroscope through a range of angles such that the selected spectrum of returned light includes a range of possible wavelengths, wherein the means for detecting include a display for displaying the intensity of the detected spectrum over the range of possible wavelengths.

4. Diagnostic and treatment apparatus for living tissues, comprising:
   a laser light generator;
   a first spectroscope optically coupled to receive laser light emitted from the laser light generator, wherein said first spectroscope selectively outputs a specific spectrum from the laser light received from the laser light generator;
   a laser light transmitting system optically coupled to receive said specific spectrum output from said first spectroscope and transmit said specific spectrum to a target area of said living tissues;
   a second spectroscope arranged to optically receive light returned from said target area of said living tissues, wherein said second spectroscope selectively outputs a spectrum from the light returned from the target area;
   means, receiving the output from the second spectroscope, for detecting the spectrum selected from light returned from said target area of said living tissues; and
   laser light irradiation means for emitting laser light from said laser light generator to irradiate said target area of said living tissues.

5. Diagnostic and treatment apparatus as in claim 2, wherein the laser light generator comprises a Nd:YAG laser.

6. Diagnostic and treatment apparatus as in claim 4, wherein the laser light irradiation means is coupled to the laser light transmitting system so as to emit the specific spectrum from the first spectroscope to irradiate the target area of said living tissues.

7. Diagnostic and treatment apparatus as in claim 4, wherein the laser light irradiation means comprise means, separate form the first spectroscope and the laser light transmitting system, for directly supplying a portion of light emitted by the laser light generator to irradiate the target area of said living tissues.

8. Diagnostic and treatment apparatus as in claim 4, further comprising means for scanning the second spectroscope through a range of angles such that the selected spectrum of returned light includes a range of possible wavelengths, wherein the means for detecting include a display for displaying the intensity of the detected spectrum over the range of possible wavelengths.

* * * * *